United States Patent [19]
Ball

[11] Patent Number: 4,925,030
[45] Date of Patent: May 15, 1990

[54] CARTRIDGE

[75] Inventor: Keith V. Ball, Burwood, Australia

[73] Assignee: Schering Agrochemicals Limited, Cambridge, England

[21] Appl. No.: 246,345

[22] Filed: Sep. 19, 1988

[30] Foreign Application Priority Data

Sep. 21, 1987 [AU] Australia ................... PI4473

[51] Int. Cl.⁵ ............................... B65D 73/00
[52] U.S. Cl. ............................. 206/487; 206/343; 206/345; 206/346; 206/483
[58] Field of Search ............ 206/3, 338, 343, 344, 206/345, 528, 532, 534.1, 538, 346, 487, 483, 347

[56] References Cited

U.S. PATENT DOCUMENTS

| | | | |
|---|---|---|---|
| 3,153,500 | 10/1964 | Pachmayr et al. | 206/3 |
| 3,428,169 | 2/1969 | Hilti | 206/343 |
| 3,693,220 | 9/1972 | Pabich et al. | 206/343 |
| 3,812,961 | 5/1974 | Merrick et al. | 206/338 |
| 4,106,618 | 8/1978 | Haytayan | 206/343 |
| 4,154,239 | 5/1979 | Turley | 128/217 |
| 4,451,254 | 5/1984 | Dinius et al. | |
| 4,531,938 | 7/1985 | Kaye et al. | |
| 4,560,061 | 12/1985 | Haytayan | 206/346 |
| 4,574,954 | 3/1986 | Reid | 206/538 |
| 4,576,591 | 3/1986 | Kaye et al. | |
| 4,720,374 | 1/1988 | Ramachandran | 206/538 |

FOREIGN PATENT DOCUMENTS

| | | |
|---|---|---|
| 0090899 | 10/1983 | European Pat. Off. |
| 840276 | 11/1958 | United Kingdom |
| 1583816 | 2/1981 | United Kingdom |

Primary Examiner—David T. Fidei
Attorney, Agent, or Firm—Randall A. Hillson

[57] ABSTRACT

A cartridge for use in transporting pellets for use in an implant gun or the like. The cartridge comprising an elongate cartridge body having an elongate carrier strip and, spaced along the carrier strip, a plurality of substantially uniformly spaced holders for respective pellets, each holder defining a respective cavity such that each holder is able to hold at least one pellet.

17 Claims, 2 Drawing Sheets

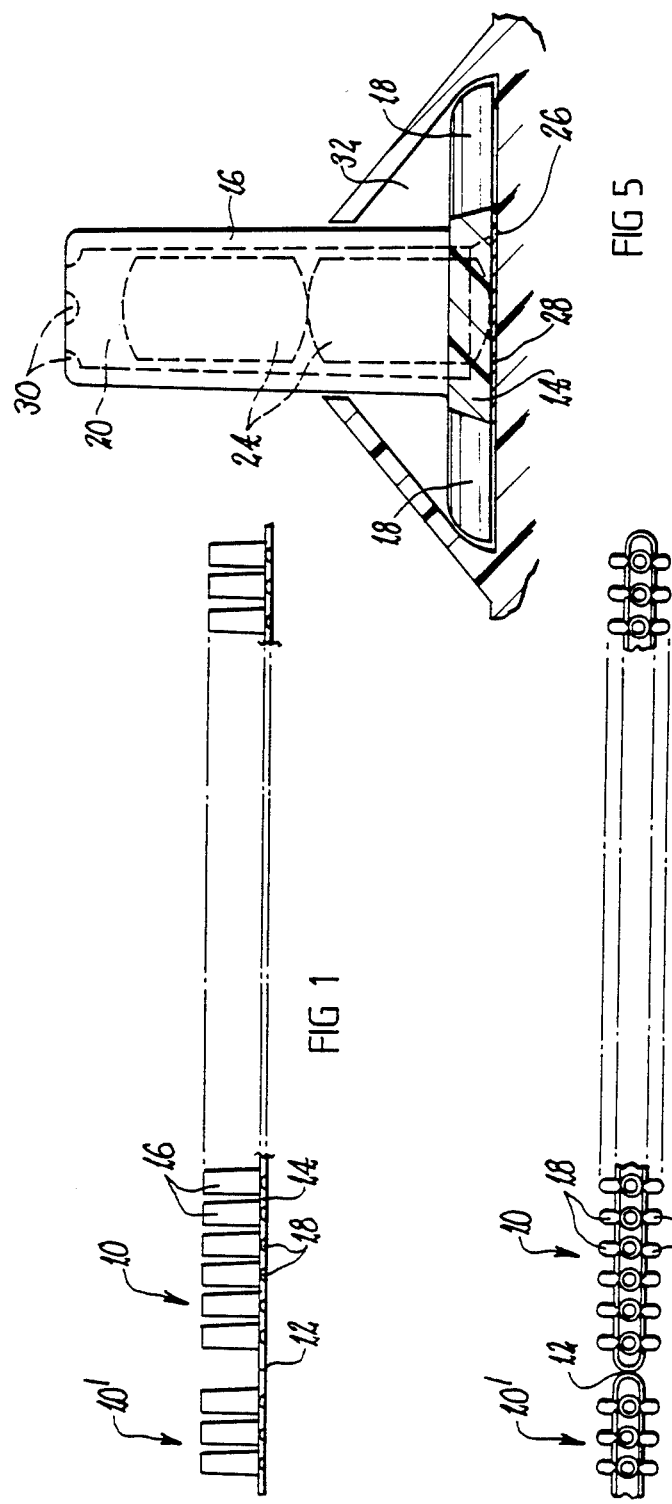

CARTRIDGE

FIELD OF THE INVENTION

This invention relates to an improved cartridge for transporting pellets for use in an implant gun or the like, and to a supply of pellets provided in such cartridge for a gun.

BACKGROUND OF THE INVENTION

In a variety of types of guns, such as an implant gun as disclosed in our co-pending Australian patent application PI 4456 filed 18 Sept. 1987 (co-pending U.S. application Serial No. 246,344 filed 19 Sept. 1988), there is a need for a devide in which pellets or the like are transportable in turn to a discharge position. The present invention is directed to providing an improved cartridge for this purpose, and to a cartridge/pellets assembly.

SUMMARY OF THE INVENTION

A cartridge according to the invention comprises an elongate cartridge body, having an elongate carrier strip and, spaced along the carrier strip, a plurality of substantially uniformly spaced holders for respective pellets, each holder defining a respective cavity such that each holder is able to hold at least one pellet.

The cartridge body preferably is flexible, such as by being formed from a suitable plastics material. Low density polyethylene or a similar grade of polypropylene are particularly suitable. However, other plastics materials with similar physical properties can be used.

The strip preferably is of flat, ribbon form. The holders preferably are provided on one major face of the strip, and most preferably are centrally disposed on such face, and uniformly spaced therealong.

The cavities, and most preferably the holders externally, preferably are configured so as to conform substantially to at least one section of the pellets. The pellets most conveniently are of substantially circular cross-section in at least one plane, such as being of spherical or cylindrical form. The cavity of each holder, for such pellets, most preferably is of substantially cylindrical form.

Each holder has at least one opening communicating with its cavity, to enable at least one pellet to be inserted into or ejected from the cavity. Preferably, each holder has two opposed openings, each communicating with its cavity; one opening enabling access of a pellet ejecting device, such as an ejecting pin, through which such device can extend to eject the pellet or pellets through the other opening.

In one convenient form of cartridge according to the invention, each holder is of cylindrical form and has its axis perpendicular to the strip. Where the strip is of flat ribbon form, the holders preferably are perpendicular to a major face thereof. In such form, each holder may be hollow and has each end open; with access to the end thereof adjacent the strip being provided by a respective opening through the strip.

In such form, each holder and its cavity may taper slightly away from the strip. This facilitates production of the cartridge, which most preferably is formed by injection moulding of a suitable thermoplastics material. For the same reason, but also to facilitate insertion of pellets into the holders, the openings in the strip may be of counter-sunk form at the major face of the strip remote from the holders. Also, the opening of the holders remote from the strip may be partially obstructed, such as by provision of a marginal flange. Alternatively, a number of small protruberances can be formed around that opening.

The holders, after at least one pellet is provided in each, may be at least partially closed. Thus, where the holders are of the above-described slightly tapered form, a thin film or foil may be applied over the remote face of the strip to retain the pellets therein. Such film or foil most preferably is readily able to be perforated, and may be heat sealed or adhesively bonded to the strip. Alternatively, an opening to each cavity adjacent the strip may be partially closed by a marginal flange or protruberances past which the pellets are forced into each cavity; the flange or protrubances being able to recover resiliently to retain the pellets in the cavity.

BRIEF DESCRIPTION OF THE DRAWINGS

In order that the invention may more readily be understood, reference now is directed to the accompanying drawings, in which:

FIGS. 1 and 2 show, in side elevation and top plan view, cartridges of typical approximate actual size, as formed by injection moulding for use with an implant gun as described in our above-described co-pending Australian patent application PI 4456 (U.S. Ser. No. 246,344);

FIG. 5 is sectional view, taken on line V-V of FIG. 3.

DETAILED DESCRIPTION OF THE INVENTION

Figure 4:
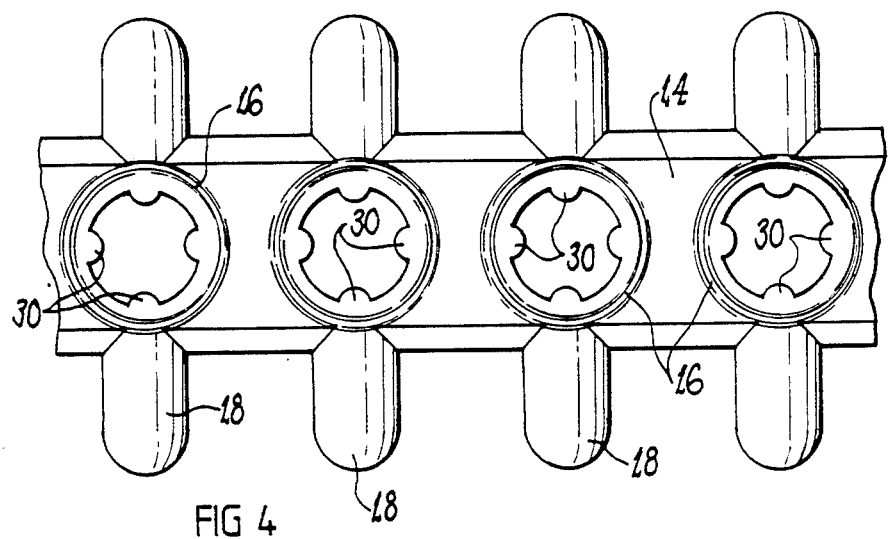
FIG. 4 is a bottom plan view of the part cartridge of FIG. 3.

The cartridge 10 of FIGS. 1 and 2 is formed by injection moulding low density polyethylene. Typically an end to end connected series of cartridges are formed simultaneously, part of a second cartridge 10' being shown in each of FIGS. 1 and 2. After moulding, the cartridges readily are able to be separated by rupturing the thin bridging elements 12 therebetween.

Cartridge 10 has a thin basal strip 14, from one face of which projects a series, typically of about 20 or 25, of pellet holders 16. To each side of each holder 16, strip 14 has a respective laterally projecting guide tab 18.

Figure 3:
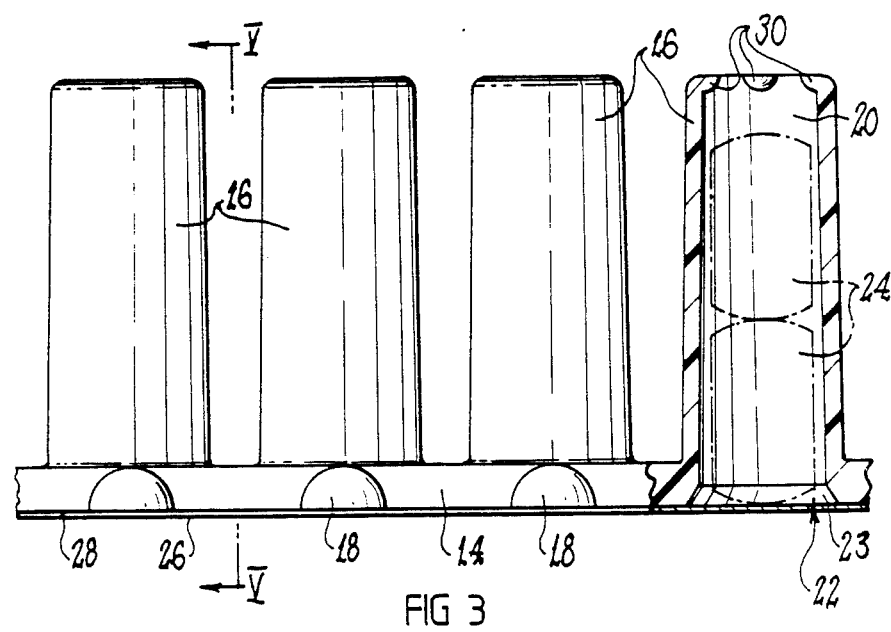
FIG. 3 is a view, in side elevation, of part of the cartridge of FIG. 1, on a scale of about 10:1.

As shown in FIG. 3; holders 16 are of hollow, substantially cylindrical form. However, each tapers slightly away from strip 14.

The cavity 20 of each holder 16 communicates with a respective opening 22 in strip 14; with each opening having a flared inlet 23 thereto.

Cartridge 10 is intended to hold two cylindrical pellets 24 in each holder 16. Such pellets 24 are shown in broken outline at the time of insertion into the holder 16 shown in section in FIG. 3. After the pellets 24 are inserted into each holder 16, openings 22 are closed by application of a thin, perforatable layer 26 of plastics film, metal foil, or a laminate material over bottom surface 28 of strip 14. Layer 26 is shown as if applied to surface 28 but, obviously, it is applied, such as by heat sealing or adhesive bonding, after insertion of the required pellets 24.

The end of holders 16 remote from strip 14 is configured to retain pellets 24 therein. For this purpose, a number of radially inwardly projecting protruberances 30 are provided around cavity 20. The radial extent of protuberances 30 is such that they prevent inadvertent passage of pellets 24, but enable the latter to be ejected by a moderate force. This arrangement is sufficient where the pellets do not require protection from air and/or moisture. However, where such protection is required, a thin membrane can be provided across that remote end of cavity 20. Such membrane can be additional to, or instead of, protruberances 30. The membrane can be produced as part of cartridge 10 by injection moulding. Alternatively, the membrane may comprise a thin film or foil applied across the remote end of holders 16, such as by heat sealing an adhesive bonding.

In use of cartridge 10 is an implant gun of our above-described co-pending application, it is inserted end-wise into a guideway 32 of a pellet discharge device, such as an implant gun as disclosed in our above-mentioned Australian patent application PI 4456 (U.S. Ser. No. 246344). As shown, guideway 32 has a form somewhat complementary to that of the cartridge as shown in FIG. 5. The cartridge is then indexed along the guideway 32, to present each holder and its pellet(s) in turn to a discharge position of such device. Guide tabs 18 enagle such indexing under the action of an indexing means, such as a pair of ratchet wheels, engageable with tabs 18. An ejecting pin then is inserted through the opening 22 of a holder at such position, perforating the film or foil 26 of the holder, to eject the pellet(s) through protruberances 30. Tabs 18 assist is guiding cartridge 10 along guideway 32. However, they also facilitate bending of cartridge 10 around any curve in guideway 32 and, more importantly, they enable indexing means to engage cartridge 10 and to impart indexed, endwise movement to cartridge 10.

The pellets can be of a wide variety of forms. In one form, they are for implantation into or below animal tissue, and may comprise a variety of drugs, trace elements or like materials.

Finally, it is to be understood that various alterations, modifications and/or additions may be introduced into the constructions and arrangements of parts previously described without departing from the spirit or ambit of the invention.

The claims defining the invention are defined as follows:

1. A cartridge adapted for use in transporting pellets for use in an implant gun and enabling at least one pellet to be ejected from the cartridge and dispensed by the gun in each successive actuation of the gun, the cartridge comprising:
   (a) an elongate cartridge body having an elongate carrier strip with first and second major faces; and,
   (b) spaced along and formed integrally with the carrier strip, a plurality of substantially uniformly spaced holders for respective pellets, each holder defining a respective cavity such that each holder is able to hold at least one pellet for transport through said implant gun;
   (i) wherein each holder projects perpendicularly from the first major face of the strip, along an axis of said holder extending away from said second major face;
   (ii) each holder having first and second opposed openings communicating with said cavity, with the first opening of each holder being defined at an end thereof remote from said strip and the second opening thereof comprising a respective opening through said strip and accessible from said second major face of said strip; and,
   (iii) wherein said strip has a plurality of integrally formed tabs therealong at a spacing between successive tabs substantially corresponding to the spacing between the axes of successive said holders, said tabs providing means by which said cartridge body can be indexed along a guideway and projecting laterally from at least one side of said strip with respect to said major faces and the axes of said holders.

2. A cartridge according to claim 1, wherein the strip is of flat, ribbon form.

3. A cartridge according to claim 2, wherein the holders are substantially centrally disposed on said strip and substantially uniformly spaced thereon.

4. A cartridge according to claim 3, wherein each holder is of substantially cylindrical form.

5. A cartridge according to claim 4, wherein the first opening of each holder provides a partial obstruction for said cavity at an end thereof remote from the strip.

6. A cartridge according to claim 5, wherein the first opening of each holder partially obstructs said cavity by provision of a marginal flange.

7. A cartridge according to claim 5, wherein the first opening of each holder partially obstructs said cavity by provision of a plurality of small protuberances spaced around that opening.

8. A cartridge according to claim 1, wherein said second opening is dimensioned to enable at least one pellet to be inserted into the cavity.

9. A cartridge according to claim 8, wherein said second opening enables access for a pellet ejecting device through which said device can extend to eject the at least one pellet through the first opening.

10. A cartridge according to claim 1, wherein the second opening in said strip for each cavity is of countersunk form at said second major face of the strip remote from the holders.

11. A cartridge according to claim 1, wherein the second opening in said strip are covered by a thin layer of material provided over said second face thereof readily able to be perforated to enable access therethrough to the cavity of respective holders.

12. A cartridge according to claim 1, wherein respective said tabs are provided along each side of said strip.

13. A cartridge according to claim 1, wherein the second opening in said strip are covered by a thin layer of material provided over said second face thereof readily able to be perforated to enable access therethrough to the cavity of respective holders.

14. A cartridge according to claim, wherein the body is flexible and is formed from a plastics material selected from low density polyethylene and polypropylene.

15. A cartridge according to claim 1, wherein the cavity of each holder is configured so as to conform substantially to at least one cross-section of the pellets.

16. A cartridge according to claim 15, wherein the cavity of each holder is of substantially cylindrical form.

17. A cartridge according to claim 1, wherein at least one pellet is provided in the cavity of each holder.

* * * * *

UNITED STATES PATENT AND TRADEMARK OFFICE
CERTIFICATE OF CORRECTION

PATENT NO. : 4,925,030

DATED : May 15, 1990

INVENTOR(S) : Keith V. Ball

It is certified that error appears in the above-identified patent and that said Letters Patent is hereby corrected as shown below:

In Column 1, line 15, delete "devide" and insert therefor --device--.

In Column 3, line 43, delete "defined".

Signed and Sealed this

Twenty-ninth Day of September, 1992

Attest:

DOUGLAS B. COMER

Attesting Officer

Acting Commissioner of Patents and Trademarks